United States Patent [19]

von Blücher et al.

[11] Patent Number: 5,612,300

[45] Date of Patent: Mar. 18, 1997

[54] MICROEMULSION FOR THE DECONTAMINATION OF ARTICLES CONTAMINATED WITH CHEMICAL WARFARE AGENTS

[76] Inventors: Hasso von Blücher, Parkstrasse 10, D-40699 Erkrath; Ernest de Ruiter, Höhenstrasse 57A, D-51381 Leverkusen, both of Germany

[21] Appl. No.: 309,450

[22] Filed: Sep. 20, 1994

[30] Foreign Application Priority Data

Aug. 13, 1994 [DE] Germany .......................... 44 28 793.3

[51] Int. Cl.⁶ .............. A62D 3/00; B01J 13/00; C11D 1/14

[52] U.S. Cl. .............. 510/110; 252/312; 510/417; 588/200; 588/901

[58] Field of Search .............. 252/312, 550, 252/DIG. 6, DIG. 14; 588/200, 901; 210/643; 510/110

[56] References Cited

U.S. PATENT DOCUMENTS

| | | | |
|---|---|---|---|
| H366 | 11/1987 | Seiders | 252/312 |
| 3,617,546 | 11/1971 | Li et al. | 210/638 |
| 3,810,788 | 5/1974 | Steyermark | 134/42 |
| 3,976,582 | 8/1976 | Douglas et al. | 252/312 X |
| 4,146,499 | 3/1979 | Rosano | 252/312 X |
| 4,472,291 | 9/1984 | Rosano | 252/312 X |
| 4,555,343 | 11/1985 | Bauer et al. | 210/643 |
| 4,587,106 | 5/1986 | Bauer et al. | 210/643 X |
| 4,971,707 | 11/1990 | Osterloh | 252/312 X |
| 5,236,614 | 8/1993 | Jacquet et al. | 252/DIG. 14 |
| 5,294,644 | 3/1994 | Login et al. | 252/357 X |

*Primary Examiner*—Richard D. Lovering
*Attorney, Agent, or Firm*—Cohen, Pontani, Lieberman, Pavane

[57] ABSTRACT

A method is described for the decontamination of equipment contaminated with chemical warfare agents. The warfare agents are not destroyed by aggressive chemicals, as is usual, but instead are extracted using a microemulsion and rinsed off.

1 Claim, No Drawings

MICROEMULSION FOR THE DECONTAMINATION OF ARTICLES CONTAMINATED WITH CHEMICAL WARFARE AGENTS

BACKGROUND OF THE INVENTION

1. Field of the Invention

The present invention concerns a method of using a microemulsion to detoxify articles contaminated with chemical warfare agents.

2. Description of the Related Art

The introduction of chemical warfare agents went hand in hand not only with the need for protection but also with the need for a possible method of decontaminating articles and persons which had been contaminated, i.e. of destroying or washing off adhering warfare agents. Articles to be decontaminated range from protective masks to aircraft. The fundamental methods are chemical, based predominantly on oxidation or hydrolysis, and physical, involving soap, water and solvent. In addition the contamination of permeable protective suits, which always contain active charcoal, requires relatively high temperatures in order to desorb the warfare agents from the charcoal.

The requirements placed on a decontamination method can be summarized as follows:

1. The subjects treated should not be damaged.
2. The decontamination agent should be nonpolluting and non-toxic to humans.
3. The products employed should not be readily flammable, either individually or in the mixture employed.
4. Application should be possible under all conceivable conditions, including those of temperature (31 20° C. to 55° C.).
5. High storage stability of the individual components, and good stability of the ready-to-use mixture.
6. The logistical problems should be minimal.

In the case of the methods often based on chlorinated lime currently used in the NATO sector, these requirements are in some cases no more than wishful thinking. Although the warfare agents are destroyed, application is relatively simple and the products used in these methods are inexpensive, oxidative decontamination methods are highly corrosive, for which reason they cannot be used, for example, for aircraft, sensitive equipment (.e.g. radio equipment), motor-vehicle interiors, etc.; they readily remove fresh alkyd resin coatings, have a sometimes inadequate effect against poisons which have penetrated more deeply, and the chemicals used are neither nonpolluting nor easy to store. The composition of C-8 emulsion is:

7.5% calcium hypochlorite
15% perchloroethylene or carbon tetrachloride
1% emulsifier
76.5% water Moreover, in the USA and many western countries the DS 2 solution is used which, because of its chemical composition—2% concentrated sodium hydroxide solution, 70% diethylenetriamine and 28% ethylene glycol monomethyl ether—is classified not only as extremely aggressive but also as a fire hazard.

SUMMARY AND DETAILED DESCRIPTION OF THE INVENTION

It is therefore the object of the present invention to provide a method of decontamination which does not have the disadvantages of this highly aggressive method.

The method according to the invention makes use of a microemulsion which extracts or detaches the warfare agents, i.e. a physical process. The warfare agents are washed off in a highly diluted form, and—even without specific chemical destruction—are degraded after a while by hydrolysis, whether in the soil or in collection tanks. Of course, it is also possible to carry out chemical destruction of the warfare agents in these tanks using chlorinated lime.

The term emulsion is appropriate when an oily phase is dispersed in an aqueous phase, or vice versa. In such emulsions the droplets usually have diameters of 1–10 µm. Emulsions possess a free energy which is proportional to the area between the phases. The finer the emulsion, the greater the free energy. (Thus energy [stirring, shaking] is required in order to prepare an emulsion.) For this reason emulsions are not thermodynamically stable; they tend to become less and less fine, since in this process the interphase area is reduced. Droplet growth occurs by coalescence or mass transport. This coalescence of the droplets can be prevented by adding emulsifiers or stabilizers. The latter are both oleophilic and hydrophilic and envelope the droplets with a protective skin.

In contrast to conventional emulsions, microemulsions are of low turbidity as a result of the much lower droplet size (60–200 Å). The major difference, however, is that they are thermodynamically stable and that their preparation does not require additional energy (e.g. stirring). Their properties are independent of the preparation process. In this context, ionic wetting agents (e.g. a soap) are normally required together with nonionic "cosurfactants", usually a higher alcohol.

The proposed microemulsion contains an oily phase, an emulsifier, a co-emulsifier, a soap and a large quantity of water (up to 94%!). All the components are readily biodegradable and conform to current conceptions regarding environmental protection.

Subsequent rinsing with water, while desirable, is by not means necessary.

A typical formulation is:

Oily phase: 0.7% dodecane

Emulsifier: 2.1% SDS (sodium lauryl sulphate)

Coemulsifier: 2.9% hexanol

Wetting agents: 0.5% FSO-100 (Du Pont)

Water: 94%

In order to achieve improved frost resistance it is possible to add NaCl and antifreeze agents. A typical formulation which can be employed down to about −10° C. is:

Water 87.23%

Dodecane 0.65%

SDS (emulsifier) 1.94%

Hexanol (coemulsifier) 2.68%

FSO-100 (wetting agent) 0.46%

NaCl 3.5%

TX-100 4.0%

A further improvements in frost resistance can be achieved, of course, by additional antifreeze components. However, it should not be forgotten here that every reduction in the temperature slows down the decontamination process; however, this also applies to chemical decontamination methods.

The preparation of the microemulsion under field conditions is extremely simple, since for 1000 l of microemulsion only 50–60 l of the mixture of the nonaqueous components need be carried. The water is subject to no particular requirements, and even pond water is suitable. The high water content of the emulsion means holding only low stocks of products which are in any case unobjectionable.

Because of the unobjectionable nature of the products, detoxifications for training purposes can be carried out without any problems.

In order to enable the warfare agents to be extracted with the microemulsion, a certain contact time is required which depends on the material to be contaminated, on the depth of penetration, etc. Comparative investigations with chemical methods have shown (see below) that the time required for them to act must be fairly similar. This is not surprising, since it is the first step in all the methods, namely the extraction, which is the rate-determining factor. The contact time required can be brought about either by repeated spraying or by increasing the viscosity (addition of a smaller quantity of water). The latter measure is particularly necessary, or at least useful, in the detoxification of smooth, vertical or inclined areas.

The microemulsion according to the invention is primarily intended for the detoxification of equipment and weapons systems. However, whereas the conventional, aggressive decontamination agents cannot be used for sensitive equipment and aircraft (damage to the electronics, for example), in these cases detoxification can be carried out using the microemulsion without concern.

Since the microemulsion can be classified as nontoxic, it is also possible to decontaminate wearers of contaminated, impermeable protective suits before the suits are removed.

The material to be decontaminated commonly has a coating based on alkyd resins and/or polyurethanes. Warfare agents penetrate the coating layer. In order to compare the microemulsion according to the invention with the chemical methods used nowadays, therefore, panels of steel plate were coated with an alkyd or PU coating material and, after curing, were contaminated with mustard gas and VX (10 g/m$^2$). The contaminated areas were covered with a Teflon plate in order to make optimum use of the penetration time (3 h). The panels were then decontaminated in the horizontal and in the vertical position. Action time: 30 min. After decontamination had been carried out the panels were extracted for 24 h using a mixture of hexane and isopropyl alcohol, and the warfare agents in the extract were determined by gas chromatography.

The results are summarized in Table 1.

TABLE 1

Comparison of conventional methods with the microemulsion:

| Test panels: | metal with alkyd coating material |
| Warfare agent: | mustard gas (a) and VX (b), each at 10 g/m$^2$ |
| Action time: | 3 h |

| | Effectiveness % | |
| Method | horizontal | vertical |
| --- | --- | --- |
| Chlorinated-lime bleach | (a) 65 | (a) 62 |
| | (b) 96.8 | (b) 90.1 |
| C-8 emulsion | (a) 88 | (a) 84 |
| | (b) 99.1 | (b) 99.4 |
| Microemulsion | (a) 93 | (a) 70 |
| | (b) 99.8 | (b) 96.3 |

Despite these good test results it should not be overlooked that the microemulsion has disadvantages as well as advantages. Therefore, any potential user should weigh the advantages against the disadvantages, taking into account the area of application.

The low quantities of non-hazardous products to be stored are a decisive advantage from the point of view of logistics.

Since the products are environmentally compatible, no secondary damage need be feared in the case of accidents (leaks) and training exercises. Since the microemulsion is not aggressive, sensitive systems and even persons can be detoxified. In this context the chemical detoxification methods are disadvantageous without a doubt.

A disadvantage of the microemulsion is its sensitivity to frost: water freezes at 0° C. Although the freezing point can be lowered, by adding antifreeze, $CaCl_2$ or NaCl, to about −10° C., or −20° C. in extreme cases, it is likely that the effectiveness, which is in any case somewhat lower at lower temperatures, will be further reduced by this measure. This may hinder somewhat application in northern countries, at least during the cold seasons.

It must be regarded as a disadvantage that the warfare agents are not destroyed but remain in the soil until their hydrolytic degradation, unless the emulsion which runs off is collected in tanks.

Finally, it should not be overlooked that the decontamination with the microemulsion is somewhat less effective than with chemical agents, especially on inclined and vertical areas. The increase in the viscosity which has already been mentioned and can be achieved by using a smaller quantity of water is usually a remedy to this.

The guideline formulations given indicate which compositions can be regarded as optimum for most cases. In this context it is not only the absolute quantities which have an effect but also the ratio of the components to one another. These guideline formulations should therefore not be regarded as a restriction, since the person skilled in the art, having grasped the teaching of the patent, can vary each component within certain limits in order to achieve results which, in particular cases, may be even better.

In this regard some information may be useful:

a) Influence of the water content

This has been varied from 85–97%. At horizontal smooth surfaces in particular a decrease in effectiveness has been observed at an extremely high water content (=little of the organic components). At vertical surfaces the wetting properties and/or the contact surface of the micelles of the microemulsion are likely to have an increased influence on the efficiency.

b) Influence of the hexanol content

This has been varied from 0–7%. It appears that the hexanol performs the active role in the extraction of the warfare agents.

c) Influence of the dodecane content

This has been varied from 0.3–2% without any notable influence on the effectiveness of the microemulsion.

d) Influence of the SDS content

The SDS content has been varied from 0.5 to 4%.

Especially in the case of vertical surfaces an improved wetting capability is noticeable and of advantage. For this reason the action of the SDS has also been intensified by adding 0.1 to 1%, preferably 0.5% of FSO-100, a typical wetting agent from the so-called Zonyl family.

We claim:

1. A method of decontaminating equipment and persons contaminated with chemical warfare agents comprising the use of a non-oxidizing microemulsion, said microemulsion consisting essentially of 85–97% water, 0.1–3.5% of a dodecane oily phase, 0.5–4% of sodium lauryl sulfate emulsifier, 0.5–7% of hexanol co-emulsifier and 0.1–1% of a wetting agent mixture of monoether reaction products of a mixture of perfluoroalkyl alcohols with ethylene oxide, polyethylene glycol and 1,4-dioxane, wherein said alkyl groups are $C_2$ to $C_{20}$.

* * * * *